United States Patent [19]

Sunkel et al.

[11] Patent Number: 5,298,619
[45] Date of Patent: Mar. 29, 1994

[54] 1,4-DIHYDROPYRIDINE COMPOUNDS WITH PAF-ANTAGONISTIC ACTIVITY

[75] Inventors: Carlos Sunkel; Miguel Fau de Casa-Juana; Luis Santos; Pilar Ortega; Jaime Priego, all of Madrid, Spain

[73] Assignee: Alter, S.A., Madrid, Spain

[21] Appl. No.: 924,319

[22] Filed: Aug. 3, 1992

[30] Foreign Application Priority Data

Sep. 9, 1991 [ES] Spain .............................. 91500103

[51] Int. Cl.$^5$ .............................. C07D 211/86
[52] U.S. Cl. .............................. 544/124; 546/283; 546/322
[58] Field of Search ............ 546/322, 283; 544/124

[56] References Cited

PUBLICATIONS

Sunkel, *Journal of Med. Chem.*, vol. 33, No. 12, Dec. 1990, pp. 3205–3210.
Sunkel, *Chem. Abstracts*, vol. 111, No. 25, Abstract No. 232,582e, Dec. 18, 1989, p. 767.
Ortega et al., *J. of Pharm. & Exp. Ther.*, vol. 255, No. 1, 1990, pp. 28–33.
Gallardo et al, *J. of Pharm & Exp. Ther.*: vol. 255, No. 1 1990, pp. 34–39.

*Primary Examiner*—C. Warren Ivy
*Assistant Examiner*—Zinna N. Davis
*Attorney, Agent, or Firm*—Darby & Darby

[57] ABSTRACT

4-alkyl-1,4-dihydropyridines with activity antagonistic of the PAF-"acether" of formula (I) are described, in which R is a saturated alkyl chain C1-2; R' is a saturated or unsaturated C1-16 lineal, branched or cyclic chain that can be interrupted by an oxygen atom and can also represent a 2-(N-morpholine) ethyl group; n is 2 or 3, X is oxygen, sulphur or SO2; Ar represents an aromatic ring that cannot be phenyl when X=S and n=2. The compounds (I) can be prepared (a) by reaction of (II) with (III) and with (IV); or (b) by reacting (V) with (VI) and (IV); or (c) by reaction of (VII) with (VI). In these formulas the different radicals have the meaning given above.

Compounds of formula (I) are used for the treatment of pathologic states and disorders in which the PAF-"acether" participates, being used, for example, in treatment of inflammatory processes, psoriasis, glomerulitis, transplant rejection, acute and chronic bronchitis, bronchial asthma, states of shock and allergies Likewise it is used for the treatment of pathologic states and disorders in which it is necessary to stimulate the cellular immunity such as in immunodeficient syndromes and other situations in which the defense capacity is reduced.

$$R'-OOC\diagdown\overset{R\quad H}{\diagup}\diagdown COO-(CH_2)_n-X-Ar \qquad (I)$$
$$H_3C\diagdown\underset{\underset{H}{N}}{\diagup}\diagdown CH_3$$

$$H_3C-\underset{NH_2}{\overset{|}{C}}=CH-COO-R' \qquad (II)$$

$$H_3C-CO-CH_2-COO-(CH_2)_n-X-Ar \qquad (III)$$

$$R-CHO \qquad (IV)$$

$$H_3C-CO-CH_2-COO-R' \qquad (V)$$

$$H_3C-\underset{NH_2}{\overset{|}{C}}=CH-COO-(CH_2)_n-X-Ar \qquad (VI)$$

$$H_3C-CO-\underset{COO-R'}{\overset{|}{C}}=CH-R \qquad (VII)$$

4 Claims, No Drawings

1,4-DIHYDROPYRIDINE COMPOUNDS WITH PAF-ANTAGONISTIC ACTIVITY

TECHNICAL FIELD OF THE INVENTION

The invention is related to a series of pharmaceutical compounds containing 1,4-dihydropyridines with an alkyl group at position 4 of the ring, which possess antagonistic activity of the Platelet Activating Factor (PAF-"acether") and their methods or preparation.

BACKGROUND OF THE INVENTION

Some 1,4-dihydropyridines having an aliphatic group at position 4 of the ring, show a strong PAF-antagonistic activity not described until now (German Patent DE 3,801,717, 24th May 1989).

Surprisingly, the modulation of the side-chain at position 3 of the said ring has led to new molecules with antagonistic activity of the PAF receiver, having greater specificity, power and a much longer duration of the effect than those described in the aforementioned patent.

The chemical structure of the PAF-"acether was identified as 1-O-hexadecyl/octodecyl-2-acetyl-sn-glycero-3-phosphocoline. This compound is a phospholipidic autacoid and a mediator of extremely potent inflammatory reactions liberated by several types of cell, human tissues and experiment animals. These cells are mainly basophile, eosinophile and neutrophile granulocytes, tissue macrophages and monocutes of the peripheral blood, platelets, glandular epithelium cells, endothelial cells and neuronic tissue. The PAF-"acether" is powerful inducer of the systemic aggregation and hypotension. This effect is due to its capacity of promoting the peripheral vasodilatation, but also influences its action over pulmonary circulation and the heart, since it produces diminution of the miocardic contractility and coronary flow. Another effect of the PAF-"acether" is that of inducing bronchoconstriction at doses 100 times lower than histamine. It has also been described that the PAF-"acether" and thus, PAF-"acether" antagonists directly and indirectly regulate the lymphocyte function.

Due to all these effects, the PAF has been described as the main mediator of immunological and inflammatory illnesses.

On this basis, specific inhibitors of biosynthesis and/or the effects of the PAF-"acether" could represent a new class of therapeutic agents, especially in pulmonary illnesses like bronchial asthma, allergic pneumonitis and adult respiratory distress, in which some PAF-"acether" antagonists have reduced or abolished anaphylactic reactions and hypersensitiveness, endotoxic shock and gastric ulcers. Also, the participation of the PAF-"acether" has been demonstrated in a series of pathologic states of an immunoallergic nature like inflammatory processes, psoriasis, glomerulonephritis and transplant rejection.

Some Ca++ antagonists also present PAF antagonistic properties, as is the case with Diltiazem and Gallopamil. However, not all the Ca++ channel blocking agents have this activity. So, the 1,4-dihydropyridines, like Nifedipina, only show a very weak activity, since the concentrations needed to obtain an effect are 1,000,000 higher than those inhibiting calcium flow in other cells and, at least, 1,000 times greater than the specific antagonists of the PAF-"acether".

The invention, therefore, is referred to a series of new 1,4-dihydropyridines corresponding to formula (i) with antagonistic activity of the PAF-"acether", to the pharmaceutical compositions that contain them and their methods of preparation:

$$R'-OOC\diagdown\diagup R\diagdown\diagup H\diagdown\diagup COO-(CH_2)_n-X-Ar \qquad (I)$$
$$H_3C\diagdown N\diagup CH_3$$
$$H$$

where:

R is a saturated alkyl chain of C1–C2 like methyl or ethyl

R' is a saturated or unsaturated alkyl chain of C1–C16, lineal, branched or cyclic, such as methyl, ethyl, isopropyl, tertiary-butyl, n-hexyl, n-hexadecyl, allyl, 1-undecenyl and cinnamyl. It can also be interrupted by an oxygen atom, like 2-methoxyethyl or tetrahydrofurfuryl and can also represent the 2-(N-morpholine) ethyl grouping n is a number that can be 2 and 3

X defines an oxygen atom (O), or sulphur (S), or a $SO_2$ grouping

Ar represents an aromatic ring such as phenyl except in those compounds having X=S and n=2. It also represents a substituted phenyl group such as 4-nitrophenyl, 4-acetylaminophenyl, 4-chlorophenyl, 3,4-dichlorophenyl, 4-methylphenyl, 4-methoxyphenyl, 3-dimethyl-aminophenyl, 4-biphenyl, 4-phenoxyphenyl, 4-benzylphenyl, 4-benzyloxyphenyl. It can also represent the 1-naphthyl and 2-naphthyl groups.

The pharmacological activity of compounds of formula (I) have been established as is indicated later on.

The compounds can be obtained using known methods already described in the literature:

METHOD A

A compound of formula (II)

$$H_3C-\underset{\underset{NH_2}{|}}{C}=CH-COO-R'$$

where R' has been defined above, is made to react with a compound of formula (III)

$$H_3C-CO-CH_2-COO-(CH_2)_n-X-Ar$$

where n, X and Ar have been previously defined, and an aldehyde of formula (IV)

$$R-CHO$$

where R has been defined above, giving a compound of formula (I) or

METHOD B

A compound of formula (V)

$$H_3C-CO-CH_2-COO-R'$$

where R' has been defined above, is made to react with a compound of formula (VI)

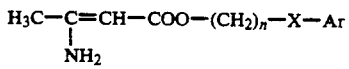

where n, X and Ar have beet defined above, and an aldehyde of formula (IV), where R has already been defined, giving a compound of formula (I) or

METHOD C

A compound of formula (VII)

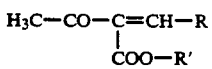

where R and R' have been defined above, is made to react with a compound of formula (VI), where n, X and Ar have been described above, giving a compound of formula (I)

The invention also refers to those process methods where one starts from a compound obtainable as an intermediate in any stage of the process and the remaining process stages are completed or the process is interrupted in any stage, or in which a starting product is prepared under the reaction conditions or in which a reactant is presented as its salts.

The mixtures of diastereoisomers or enantiomers obtained, can be separated thanks to the different physical chemical properties of the components, by means of known methods, like for example fractionated recrystallization and/or chromatography, by reactions of asymmetric induction or by the use of microorganisms.

The starting compounds are known or in the case of being new, they can be obtained following known methods.

The new compounds can be used as drugs to be administered orally, parenterally or rectally as a pharmaceutical preparation, containing one of the compounds of formula (I) in combination with an acceptable pharmaceutical excipient. The pharmaceutical preparations can be presented, for example, as tablets, pills, capsules, injectables, suppositories or in the liquid form as a syrup. Usually the amount of active compound is between 0.1 and 99% by weight of the preparation, preferable between 2 and 50% by weight in oral preparations.

The daily dose of the active substance depends on the type of administration. Generally, from 50–100 mg/day are administered orally.

PREPARATION METHODS OF THE INVENTION

The following examples illustrate the present invention without limiting it in any way.

EXAMPLE 1 (METHOD A)

Preparation of 3-(4-chlorophenylthio) propyl 5-methoxycarbonyl-2,4,6-trimethyl-1,4-dihydropyridine-3-carboxylate.

A solution composed of 9 g (0.03 mol) of 3-(4-chlorophenylthio) propyl acetylacetate, 3,56 g (0.03 mol) of methyl 3-aminocrotonate and 1.9 ml (1.49 g; 0.034 mol) of a acetaldehyde in 40 ml. of absolute ethanol, is refluxed with stirring for 7 hours. After the said time, the solvent is evaporated at reduced pressure and the residue obtained is dissolved in 15 ml of boiling ethyl acetate. The resulting solution is stirred at room temperature and afterwards it is cooled to −10° C. The solid obtained is recrystallized in methanol finally producing a yellow solid of Melting Point=99°–101° C. The yield of the reaction is 68%.

EXAMPLE 2 (METHOD A)

Preparation of 2-(4-methylphenylsulphonyl) ethyl 5-methoxycarbonyl-2,4,6-trimethyl-1,4-dihydropyridine-3-carboxylate.

A solution composed of 8.5 g (0.03 mol) of 2-(4-methylphenylsulphonyl) ethyl acetylacetate, 3.45 g (0.03 mol) of methyl 3-aminocrotonate and 1.67 ml (0.03 mol) of acetaldehyde in 30 ml of absolute ethanol, is heated to reflux with stirring during 8 hours. After said time, the solvent is evaporated at reduced pressure and the residue obtained is dissolved in 10 ml of boiling methanol. Lastly, the resulting solution is stirred at 0° C. and the solid obtained is recrystallized in methanol resulting in a white solid of Melting Point=96°–100° C. The yield of the reaction is 45%.

EXAMPLE 3 (METHOD A)

Preparation of 3-(4-phenylphenoxy) propyl 5-methoxycarbonyl-2,4,6-trimethyl-1,4-dihydropyridine-3-carboxylate.

A solution composed of 10.9 g (0.035 mol) of 3-(4-phenylphenoxy) propyl acetylacetate, 4 g (0.035 mol) of methyl 3-aminocrotonate and 1.95 ml (0.35 mol) of acetaldehyde in 35 ml of absolute ethanol is heated to reflux with stirring during 8 hours. After said time 20 ml of solvent is evaporated at reduced pressure and the resulting solution is left to cool at room temperature. In this way a solid is obtained which is recrystallized in acetonitrile, finally giving a white solid of Melting Point=133°–5° C. The yield of the reaction is 74%.

EXAMPLE 4 (METHOD A)

Preparation of 3-(4-methylphenylthio) propyl 5-methoxycarbonyl-2,4,6-trimethyl-1,4-dihydropyridine-3-carboxylate.

A solution composed of 9 g (0.034 mol) of 3-(4-methylphenylthio) propyl acetylacetate, 3.9 g (0.034 mol) of methyl 3-aminocrotonate and 2.26 ml (1.76 g; 0.040 mol) of acetaldehyde in 45 ml of absolute ethanol is heated to reflux with stirring during 7 hours. After said time, the solvent is evaporated at reduced pressure and the residue obtained is dissolved in 10 ml of boiling isopropyl ether. Afterwards, the resulting solution, is stirred at room temperature until the complete solidification of the product. Lastly, the solid so obtained is recrystallized in isopropyl ether resulting in a solid of Melting Point=80°–2° C. The yield of the reaction is 49%.

EXAMPLE 5 (METHOD A)

Preparation of 2-(phenylsulphonyl) ethyl 5-methoxycarbonyl-2,4,6-trimethyl-1,4-dihydropyridine-3-carboxylate.

A mixture composed of 30 g (0.11 mol) of 2-(phenylsulphonyl) ethyl acetylacetate, 12.78 g (0.11 mol) of methyl 3-aminocrotonate and 6.5 ml (5.07 g; 0.12 mol) of acetaldehyde in 110 ml of absolute ethanol is heated to reflux with stirring during 8 hours. After said time, the solvent is evaporated at reduced pressure and the residue obtained is dissolved in 25 ml of boiling diisopropyl ether. Afterwards, the resulting solution, is cooled to −10° C. overnight. In this way, a yellow solid is obtained which is recrystallized in n-hexane/ethyl acetate (1:1), finally resulting in a product of Melting Point = 118°-20° C. with a yield of 75%.

EXAMPLES 6-151 (METHOD A)

The compounds of Table 1 were prepared in an analogous way to that indicated in the aforementioned examples 1-5.

TABLE 1

| Example No. | R | R' | n | x | Ar | M.P.[a] (°C.) | Yield[b] (%) |
|---|---|---|---|---|---|---|---|
| 6 | $CH_3$ | $CH_3$ | 3 | O | Ph | 97–100[c] | 45 |
| 7 | $CH_3$ | $CH_3$—$CH_2$ | 3 | O | Ph | 11–3[c] | 76 |
| 8 | $CH_3$ | $(CH_3)_2$—CH | 3 | O | Ph | 120–2[d] | 65 |
| 9 | $CH_3$ | $(CH_3)_3$—C | 3 | O | Ph | 101–2[e] | 30 |
| 10 | $CH_3$ | $(CH_3)_2$—CH | 3 | S | Ph | 77–9[f] | 35 |
| 11 | $CH_3$ | $CH_2$=CH—$CH_2$ | 3 | O | Ph | 69–72[f] | 40 |
| 12 | $CH_3$ | $CH_2$=CH—$CH_2$ | 3 | S | Ph | aceite | 69 |
| 13 | $CH_3$ | $CH_3$ | 3 | $SO_2$ | Ph | 114–7[d] | 30 |
| 14 | $CH_3$ | $CH_3$—$CH_2$ | 3 | $SO_2$ | Ph | 89–92[g] | 40 |
| 15 | $CH_3$ | $CH_3$ | 3 | O | 4-$NO_2$-Ph | 153–4[d] | 69 |
| 16 | $CH_3$ | $CH_3$—$CH_2$ | 3 | O | 4-$NO_2$-Ph | 133–5[d] | 70 |
| 17 | $CH_3$ | $(CH_3)_2$CH | 3 | O | 4-$NO_2$-Ph | 113–5[d] | 64 |
| 18 | $CH_3$ | $CH_3$—$(CH_2)_5$ | 3 | O | 4-$NO_2$-Ph | 84–5[c] | 35 |
| 19 | $CH_3$ | M-$(CH_2)_2$[h] | 3 | O | 4-$NO_2$-Ph | 125–30[e] | 57 |
| 20 | $CH_3$ | $CH_3$—$(CH_2)_{15}$ | 3 | O | 4-$NO_2$-Ph | 104–6[g] | 38 |
| 21 | $CH_3$ | $(CH_3)_3$C | 3 | O | 4-$NO_2$-Ph | 106–g[f] | 25 |
| 22 | $CH_3$ | $CH_2$=CH—$CH_2$ | 3 | O | 4-$NO_2$-Ph | 102–5[d] | 33 |
| 23 | $CH_3$ | $CH_3$ | 3 | O | 4-AcNH-Ph | 103–5[c] | 65 |
| 24 | $CH_3$ | $CH_3$—$CH_2$ | 3 | O | 4-AcNH-Ph | 142–5[c] | 40 |
| 25 | $CH_3$ | $(CH_3)_2$—CH | 3 | O | 4-AcNH-Ph | 118–21[c] | 45 |
| 26 | $CH_3$ | M—$(CH_2)_2$ | 3 | O | 4-AcNH-Ph | 135–8[e] | 35 |
| 27 | $CH_3$ | $CH_3$—$(CH_2)_5$ | 3 | O | 4-AcNH-Ph | 55–9[c] | 24 |
| 28 | $CH_3$ | $(CH_3)_3$C | 3 | O | 4-AcNH-Ph | 101–4[c] | 49 |
| 29 | $CH_3$ | $CH_3O$—$(CH_2)_2$ | 3 | O | 4-AcNH-Ph | 75–80[c] | 24 |
| 30 | $CH_3$ | $CH_3$ | 3 | S | 4-AcNH-Ph | 72–4[c] | 26 |
| 31 | $CH_3$ | $CH_3$—$(CH_2)_{15}$ | 3 | S | 4-AcNH-Ph | 85–7[f] | 60 |
| 32 | $CH_3$ | $CH_3$—$CH_2$ | 3 | S | 4-AcNH-Ph | 63–5[i] | 24 |
| 33 | $CH_3$ | $CH_2$=CH—$CH_2$ | 3 | S | 4-AcNH-Ph | 140–2[c] | 35 |
| 34 | $CH_3$ | $CH_2$=CH—$CH_2$ | 3 | O | 4-AcNH-Ph | 98–CO3[d] | 23 |
| 35 | $CH_3$ | $CH_3$ | 3 | O | 4-Cl-Ph | 129–31[c] | 66 |
| 36 | $CH_3$ | $CH_3$—$CH_2$ | 3 | O | 4-Cl-Ph | 135–8[c] | 46 |
| 37 | $CH_3$ | $(CH_3)_2$CH | 3 | O | 4-Cl-Ph | 108–11[c] | 65 |
| 38 | $CH_3$ | $(CH_3)_3$C | 3 | O | 4-Cl-Ph | 91–3[f] | 20 |
| 39 | $CH_3$ | $CH_2$=CH—$CH_2$ | 3 | O | 4-Cl-Ph | 105–g[f] | 51 |
| 40 | $CH_3$ | $CH_3$—$CH_2$ | 3 | O | 3,4$Cl_2$-Ph | 134–6[c] | 60 |
| 41 | $CH_3$ | $CH_3$ | 3 | O | 3,4$Cl_2$-Ph | 82–4[d] | 31 |
| 42 | $CH_3$ | $(CH_3)_2$CH | 3 | O | 3,4$Cl_2$-Ph | 130–3[d] | 55 |
| 43 | $CH_3$ | $(CH_3)_3$C | 3 | O | 3,4$Cl_2$-Ph | 110–2[i] | 39 |
| 44 | $CH_3$ | $CH_2$=CH—$CH_2$ | 3 | O | 3,4$Cl_2$-Ph | 99–101[c] | 60 |
| 45 | $CH_3$ | $CH_3$ | 3 | S | 3,4$Cl_2$-Ph | 104–6[c] | 35 |
| 46 | $CH_3$ | $CH_3$—$CH_2$ | 3 | S | 3,4$Cl_2$-Ph | 63–6[f] | 24 |
| 47 | $CH_3$ | $CH_3$—$CH_2$ | 3 | O | 4-$CH_3$-Ph | 109–11[c] | 45 |
| 48 | $CH_3$ | $CH_3$ | 3 | O | 4-$CH_3$-Ph | 117–9[d] | 50 |
| 49 | $CH_3$ | $(CH_3)_2$CH | 3 | O | 4-$CH_3$-Ph | 121–3[c] | 60 |
| 50 | $CH_3$ | $(CH_3)_2$CH | 3 | O | 4-$CH_3$-Ph | 109–11[f] | 44 |
| 51 | $CH_3$ | $CH_2$=CH—$CH_2$ | 3 | O | 4-$CH_3$-Ph | 80–3[f] | 22 |
| 52 | $CH_3$ | $CH_3$ | 3 | $SO_2$ | 4-$CH_3$-Ph | 137–9[c] | 40 |
| 53 | $CH_3$ | $CH_3$—$CH_2$ | 3 | $SO_2$ | 4-$CH_3$-Ph | 139–41[d] | 18 |
| 54 | $CH_3$ | $CH_3$—$CH_2$ | 2 | $SO_2$ | 4-$CH_3$-Ph | 85–8[d] | 38 |
| 55 | $CH_3$ | $CH_3$ | 3 | O | 2-Naphthyl | 118–21[e] | 33 |
| 56 | $CH_3$ | $CH_3$—$CH_2$ | 3 | O | 2-Naphthyl | 98–100[c] | 30 |
| 57 | $CH_3$ | $(CH_3)_2$CH | 3 | O | 2-Naphthyl | 100–3[d] | 25 |
| 58 | $CH_3$ | $(CH_3)_3$C | 3 | O | 2-Naphthyl | 87–9[f] | 22 |
| 59 | $CH_3$ | $CH_2$=CH—$CH_2$ | 3 | O | 2-Naphthyl | 88–90[d] | 20 |
| 60 | $CH_3$ | $CH_3$—$CH_2$ | 2 | O | 4-$CH_3O$-Ph | 125–7[d] | 70 |
| 61 | $CH_3$ | $CH_3$ | 3 | O | 4-$CH_3O$-Ph | 80–3[c] | 31 |
| 62 | $CH_3$ | $CH_3$ | 2 | O | 4-$Ch_3O$-Ph | 107–9[d] | 60 |
| 63 | $CH_3$ | $CH_3$—$CH_2$ | 3 | O | 4-$CH_3O$-Ph | 64–6[f] | 32 |
| 64 | $CH_3$ | $CH_3$ | 2 | O | 4-Ph-Ph | 84–6[j] | 40 |
| 65 | $CH_3$ | $CH_3$—$CH_2$ | 2 | O | 4-Ph-Ph | 115–7[d] | 25 |
| 66 | $CH_3$ | $CH_3$—$CH_2$ | 3 | O | 4-Ph-Ph | 135–7[d] | 81 |
| 67 | $CH_3$ | $CH_3$ | 3 | O | 4-(Ph-$CH_2$)-Ph | 93–6[c] | 15 |
| 68 | $CH_3$ | $CH_3$—$CH_2$ | 3 | O | 4-(Ph-$CH_2$)-Ph | 93–5[e] | 15 |
| 69 | $CH_3$ | $CH_3$—$CH_2$ | 2 | O | 4-(Ph-$CH_2$)-Ph | 111–4[c] | 30 |
| 70 | $CH_3$ | $CH_3$—$CH_2$ | 3 | O | 4-(Ph-$CH_2O$)-Ph | 78–81[d] | 22 |
| 71 | $CH_3$ | $CH_3$ | 2 | O | 4-(Ph-$CH_2O$)-Ph | 121–3[k] | 15 |
| 72 | $CH_3$ | $CH_3$ | 3 | O | 4-(Ph-$CH_2O$)-Ph | 107–9[d] | 40 |
| 73 | $CH_3$ | $CH_3$—$CH_2$ | 2 | O | 4-(Ph-$CH_2O$)-Ph | 109–11[f] | 20 |
| 74 | $CH_3$ | $CH_3$—$CH_2$ | 2 | $SO_2$ | Ph | 90–3 | 88 |
| 75 | $CH_3$ | $(CH_3)_2$CH | 2 | $SO_2$ | Ph | 86–9 | 46 |
| 76 | $CH_3$ | $CH_3$ | 3 | S | 4-$NO_2$-Ph | 118–20[c] | 76 |
| 77 | $CH_3$ | $CH_3$—$CH_2$ | 3 | S | 4-$NO_2$-Ph | 84–8[c] | 47 |
| 78 | $CH_3$ | $(CH_3)_3$C | 3 | S | 4-$NO_2$-Ph | 104–6[f] | 39 |
| 79 | $CH_3$ | $CH_3O$—$(CH_2)_2$ | 3 | S | 4-$NO_2$-Ph | 65–8 | 89 |

TABLE 1-continued

| Example No. | R | R' | n | x | Ar | M.P.[a] (°C.) | Yield[b] (%) |
|---|---|---|---|---|---|---|---|
| 80 | CH₃ | CH₃—CH₂ | 2 | S | 4-(AcNH)-Ph | 135-7[i] | 29 |
| 81 | CH₃ | (CH₃)2CH | 2 | S | 4-(AcNH)-Ph | 110-2[i] | 37 |
| 82 | CH₃ | CH₃—CH₂ | 3 | S | 4-Cl-Ph | 115-7[d] | 86 |
| 83 | CH₃ | (CH₃)₂—CH | 3 | S | 4-Cl-Ph | 79-81[i] | 29 |
| 84 | CH₃ | CH₃—CH₂ | 2 | O | 3,4Cl₂-Ph | 137-9[c] | 90 |
| 85 | CH₃ | (CH₃)2CH | 2 | O | 3,4Cl₂-Ph | 134-6[c] | 78 |
| 86 | CH₃ | CH₃ | 2 | O | 3,4Cl₂-Ph | 145-7[c] | 82 |
| 87 | CH₃ | CH₃O—(CH₂)₂ | 2 | O | 3,4Cl₂-Ph | 110-2[d] | 70 |
| 88 | CH₃ | CH₃—(CH₂)₅ | 2 | O | 3,4Cl₂-Ph | 106-8[c] | 65 |
| 89 | CH₃ | (CH₃)₃C | 2 | O | 3,4Cl₂-Ph | 157-9[c] | 90 |
| 90 | CH₃ | M—(CH₂)[h]₂[h] | 2 | O | 3,4Cl₂-Ph | 106-9[c] | 75 |
| 91 | CH₃ | THF-CH₂ | 2 | O | 3,4Cl₂-Ph | 134-6[d] | 47 |
| 92 | CH₃ | CH₃—(CH₂)₁₅ | 2 | O | 3,4Cl₂-Ph | 88-90[d] | 45 |
| 93 | CH₃ | CH₂=CH—CH₂ | 2 | O | 3,4Cl₂-Ph | 120-2[c] | 81 |
| 94 | CH₃ | CH₂=CH—(CH₂)₉ | 2 | O | 3,4Cl₂-Ph | 86-7[d] | 70 |
| 95 | CH₃ | CH₃—CH₂ | 3 | S | 4CH₃-Ph | 68-71 | 57 |
| 96 | CH₃ | M-(CH₂)₂ | 3 | S | 4CH₃-Ph | 175-9dese[ll] hydrochloride | 32 |
| 97 | CH₃ | CH₃ | 2 | O | 2-Naphthyl | 115-7[c] | 63 |
| 98 | CH₃ | CH₃—CH₂ | 2 | O | 2-Naphthyl | 141-3[c] | 67 |
| 99 | CH₃ | (CH₃)2CH | 2 | O | 2-Naphthyl | 130-2[d] | 43 |
| 100 | CH₃ | CH₃O—(CH₂)₂ | 2 | O | 2-Naphthyl | 103-5[c] | 53 |
| 101 | CH₃ | CH₃—(CH₂)₅[h] | 2 | O | 2-Naphthyl | 87-9[c] | 70 |
| 102 | CH₃ | THF-CH₂ | 2 | O | 2-Naphthyl | 102-4 | 47 |
| 103 | CH₃ | CH₂=CH—CH₂ | 2 | O | 2-Naphthyl | 141-3[d] | 78 |
| 104 | CH₃ | M-(CH₂)₂[h] | 2 | O | 2-Naphthyl | 96-9 | 77 |
| 105 | CH₃ | CH₃—CH₂ | 2 | O | Ph | 91-3,5[d] | 26 |
| 106 | CH₃ | CH₃ | 3 | S | 4-CH₃O-Ph | 83-4[f] | 25 |
| 107 | CH₃ | CH₃ | 2 | O | Ph | 103-5[d] | 68 |
| 108 | CH₃ | (CH₃)2CH | 2 | O | Ph | 95-7[m] | 78 |
| 109 | CH₃ | CH₃ | 2 | O | 4-(Ph-CH₂)-Ph | 132-3[g] | 25 |
| 110 | CH₃ | CH₃ | 2 | O | 4-NO₂Ph | 185-7[d] | 66 |
| 111 | CH₃ | (CH₃)₃C | 2 | O | 4-NO₂-Ph | 170-3[d] | 80 |
| 112 | CH₃ | (CH₃)₃C | 2 | O | 2-Naphthyl | 101-3[f] | 24 |
| 113 | CH₃ | CH₃ | 2 | O | 1-Naphthyl | 134-7[c] | 75 |
| 114 | CH₃ | CH₃—CH₂ | 2 | O | 1-Naphthyl | 125-7[c] | 64 |
| 115 | CH₃ | (CH₃)2CH | 2 | O | 1-Naphthyl | 129-31[j] | 51 |
| 116 | CH₃ | CH₃O—(CH₂)₂ | 2 | O | 1-Naphthyl | 105-7[n] | 26 |
| 117 | CH₃ | CH₃—(CH₂)₅ | 2 | O | 1-Naphthyl | 106-8[c] | 55 |
| 118 | CH₃ | M-(CH₂)₂[h] | 2 | O | 1-Naphthyl | 133-5[c] | 77 |
| 119 | CH₃ | CH₃O—(CH₂)₂ | 2 | O | 4-NO₂-Ph | 130-2[d] | 68 |
| 120 | CH₃ | CH₃—CH₂ | 2 | O | 4-NO₂-Ph | 162-3[d] | 69 |
| 121 | CH₃ | (CH₃)2CH | 2 | O | 4-NO₂-Ph | 150-2[d] | 82 |
| 122 | CH₃ | CH₃—CH₂ | 2 | O | 4-Cl-Ph | 137-9[c] | 70 |
| 123 | CH₃ | (CH₃)2CH | 2 | O | 4-Cl-Ph | 139-42[d] | 75 |
| 124 | CH₃ | CH₂=CH—CH₂ | 2 | O | 4-Cl-Ph | 118-20[ll] | 24 |
| 125 | CH₃ | CH₃O—(CH₂)₂ | 2 | O | 4-Cl-Ph | 91-4[c] | 26 |
| 126 | CH₃ | (CH₃)₃C | 2 | O | 4-Cl-Ph | 111-4[d] | 50 |
| 127 | CH₃ | CH₃ | 2 | O | 4-Cl-Ph | 142-5[d] | 74 |
| 128 | CH₃ | CH₃—CH₂ | 2 | O | 4-CH₃-Ph | 115-7[c] | 59 |
| 129 | CH₃ | (CH₃)2CH | 2 | O | 4-Cl-Ph | 83-5[f] | 68 |
| 130 | CH₃ | CH₃O—(CH₂)₂ | 2 | O | 4-Cl-Ph | 69-71[f] | 59 |
| 131 | CH₃ | CH₃ | 2 | O | 4-Cl-Ph | 49-51[f] | 40 |
| 132 | CH₃ | CH₃—(CH₂)₁₅ | 2 | O | 2-Naphthyl | 80-3[d] | 30 |
| 133 | CH₃ | CH₃—CH₂ | 3 | O | 3-N(CH₃)₂-Ph | 96-9[i] | 55 |
| 134 | CH₃ | CH₃—CH₂ | 2 | O | 3-N(CH₃)₂-Ph | 130-2[d] | 50 |
| 135 | CH₃ | CH₃ | 2 | O | 3-N(CH₃)₂-Ph | 98-101[d] | 15 |
| 136 | CH₃ | CH₃O—(CH₂)₂ | 2 | O | 3-N(CH₃)₂-Ph | 112-4[d] | 44 |
| 137 | CH₃ | (CH₃)₃C | 2 | O | 3-N(CH₃)₂-Ph | 100-4[d] | 25 |
| 138 | CH₃ | (CH₃)2CH | 2 | O | 3-N(CH₃)₂-Ph | 121-2[d] | 15 |
| 139 | CH₃ | CH₃ | 3 | O | 4-PhO-Ph | 113-6[c] | 70 |
| 140 | CH₃ | CH₃ | 2 | O | 4-PhO-Ph | 75-8[f] | 35 |
| 141 | CH₃ | CH₃—CH₂ | 3 | O | 4-PhO-Ph | 98-101[c] | 80 |
| 142 | CH₃ | (CH₃)₃C | 3 | O | 4-PhO-Ph | 89-91 | 55 |
| 143 | CH₃ | CH₃—CH₂ | 2 | O | 4-PhO-Ph | 96-8[d] | 77 |
| 144 | CH₃ | (CH₃)2CH | 2 | O | 4-PhO-Ph | 93-6[d] | 75 |
| 145 | CH₃ | CH₃O—(CH₂)₂ | 2 | O | 4-PhO-Ph | 88-91[c] | 20 |
| 146 | CH₃ | (CH₃)2CH | 3 | O | 4-PhO-Ph | 121-4[c] | 61 |
| 147 | CH₃ | CH₃ | 3 | SO₂ | 4-NO₂-Ph | 191-3[c] | 25 |
| 148 | CH₃ | CH₃ | 3 | SO₂ | 4-NO₂-Ph | 144-6[d] | 46 |
| 149 | CH₃ | CH₃ | 3 | SO₂ | 3,4-Cl₂-Ph | 169-71[d] | 50 |
| 150 | CH₃ | CH₃ | 3 | SO₂ | 4-CH₃O-Ph | 140-1[c] | 25 |

TABLE 1-continued

| Example No. | R | R' | n | x | Ar | M.P.[a] (°C.) | Yield[b] (%) |
|---|---|---|---|---|---|---|---|
| 151 | CH₃ | CH₃ | 3 | O | 4-Ph-Ph | 144-6[c] | 30 |

[a] = Recrystallization solvent;
[c] = methanol;
[d] = ethanol;
[e] = isopropanol;
[f] = diisopropylether;
[g] = ethyl acetate;
[i] = acetonitrile;
[j] = n-hexane/ethyl acetate (1:1);
[l] = ethyl acetate/ethanol (1:1);
[m] = ethanol/water (2.5:1);
[n] = n-hexane/ethyl acetate (2:1).
[k] = purification by MPLC
[b] = referred to the recrystallized product
k = KEYS:
M = N-Morpholine;
THF = 2-Tetrahydrofurfuryl.

EXAMPLE 152 (METHOD B)

Preparation of 3-(2-naphthyloxy) propyl 5-ethoxycarbonyl-2,4,6-trimethyl-1,4-dihydropyridine-3-carboxylate.

A solution composed of 8-5 g (0.03 mol) of 3-(2-naphthyloxy) propyl 3-aminocrotonate, 3.82 ml (0.03 mol) of ethyl acetylacetate and 1.67 ml (0.03 mol) of acetaldehyde in 30 ml of absolute ethanol, is heated to reflux with stirring during 8 hours. After said time, 15 ml of solvent is evaporated at reduced pressure and the resulting mixture is stirred at 0° C., obtaining a white solid of Melting Point=94°-7° C. (recrystallized in ethanol). The yield of the reaction is 40%.

EXAMPLE 153 (METHOD B)

Preparation of 3-(4-nitrophenylthio) propyl 5-isopropoxycarbonyl-2,4,6-trimethil-1,4-dihydropyridine-3-carboxylate.

A solution composed of 9 g (0.03 mol) of 3-(4-nitrophenylthio) propyl 3-aminocrotonate, 5.04 g (0.03 mol) of isopropyl acetylacetate and 2.1 ml (1.58 g; 0.036 mol) of acetaldehyde in 45 ml of absolute ethanol, is heated to reflux with stirring during 7 hours. After said time, the solvent is evaporated at reduced pressure and the residue is dissolved in 16 ml of boiling ethyl acetate/n-hexane (1:1). Lastly, the resulting mixture is cooled to −10° C., obtaining a solid of Melting Point=80°-2° C. The yield of the reaction is 42%.

EXAMPLES 154–162 (METHOD B)

The compounds of Table 2 were obtained in an analogous way to that indicated in examples 152 and 153.

EXAMPLE 163 (METHOD C)

Preparation of 3-(phenylthio) propyl 5-methoxycarbonyl-2,4,6-trimethyl-1,4-dihydropyridine-3-carboxylate.

A solution composed of 5 g (0.035 mol) of methyl 2-acetyl-2-butenoate and 8.8 g (0.035 mol) of 3-(phenylthio) propyl 3-aminocrotonate in 35 ml of absolute ethanol, is heated to reflux with stirring during 10 hours. After said time, the solvent is evaporated at reduced pressure and the residue obtained is dissolved in 10 ml of boiling n-hexane/ethyl acetate (1:1). Lastly, the resulting solution is cooled to −10° C., obtaining a white solid of Melting Point=81°-2° C. (recrystallized in n-hexane/ethyl acetate (1:1)), with a yield of 45%.

EXAMPLE 164 (METHOD C)

Preparation of 3-(4-chlorophenylthio) propyl 2,6-dimethyl-4-ethyl-5-methoxycarbonyl-1,4-dihydropyridine-3-carboxylate.

A solution composed of 9 g (0-03 mol) of 3-(4-chlorophenylthio) propyl 3-aminocrotonate and 4.95 g (0.031 mol) of methyl 2-acetyl-2-pentenoate in 45 ml of absolute ethanol, is heated to reflux with stirring during 7 hours. After said time, the reaction mixture is cooled to −10° ° C., crystallizing a solid of Melting Point=10-2°-4° C. (recrystallized in ethanol). The yield of the reaction is 50%.

TABLE 2

| Ex. no | R | R' | n | x | Ar | M.P.[a] (°C.) | Yield[b] (%) |
|---|---|---|---|---|---|---|---|
| 154 | CH₃ | CH₃ | 3 | O | 1-Naphthyl | 40-3[d] | 50 |
| 155 | CH₃ | CH₂=CH—CH₂ | 3 | O | 1-Naphythyl | 96-101[c] | 19 |
| 156 | CH₃ | (CH₃)₃C | 3 | S | Ph | Oil | 74 |
| 157 | CH₃ | CH₃—(CH₂)₅ | 3 | S | 4-NO₂-Ph | 74-7[j] | 76 |
| 158 | CH₃ | CH₂=CH—CH₂ | 3 | S | 4-Cl-Ph | 55-7 | 68 |
| 159 | CH₃ | Ph-CH=CH—CH₂ | 3 | S | 4-Cl-Ph | 117-20[c] | 87 |
| 160 | CH₃ | CH₂=CH—CH₂ | 3 | S | 4-CH₃-Ph | 58-60 | 64 |
| 161 | CH₃ | Ph-CH=CH—CH₂ | 3 | S | 4-CH₃-Ph | 84-7[c] | 85 |
| 162 | CH₃ | Ph-CH=CH—CH₂ | 2 | O | 2-Naphthyl | 122-4[c] | 68 |

[a] = Recrystallization solvent;
[b] = Referred to the recrystallized product;
[c] = methanol;
[d] = ethanol;
[j] = n-hexane/ethyl acetate (1:1).

EXAMPLE 165 (METHOD C)

Preparation of 3-(4-chlorophenylthio) propyl 2,6-dimethyl-4-ethyl-5-ethoxycarbonyl-1,4-dihydropyridine-3-carboxylate.

A mixture composed of 9 g (0.031 mol) of 3-(4-chlorophenylthio) propyl 3-aminocrotonate and 5.4 g (0.031 mol) of ethyl acetyl-2-pentenoate in 45 ml of absolute ethanol, is heated to reflux with stirring during 7 hours. After said time, the solvent is evaporated at reduced pressure and the residue obtained is dissolved in 10 ml of boiling diisopropylether. In continuation, the solution so obtained is stirred at room temperature until the complete solidification of the product. In this way a solid is obtained of Melting Point=83°-6° C. (recrystallized from diisopropylether), with a yield of 69%.

EXAMPLES 166-172 (METHOD C)

The compounds of Table 3 were obtained in analogous way to that indicated in examples 163-165.

TABLE 3

| Ex. no | R | R' | n | x | Ar | M.P.$^a$ (°C.) | Yield$^b$ (%) |
|---|---|---|---|---|---|---|---|
| 166 | CH$_3$ | CH$_3$—CH$_2$ | 3 | S | Ph | 84-5$^f$ | 36 |
| 167 | CH$_3$ | CH$_3$ | 3 | S | 2-Naphthyl | 82-6$^j$ | 50 |
| 168 | CH$_3$ | CH$_3$—CH$_2$ | 3 | S | 2-Naphthyl | 62-5$^f$ | 35 |
| 169 | CH$_3$ | (CH$_3$)$_3$C | 3 | S | 4-Cl-Ph | oil | 35 |
| 170 | CH$_3$ | (CH$_3$)$_3$C | 3 | S | 4-CH$_3$-Ph | oil | 35 |
| 171 | CH$_3$—CH$_2$ | CH$_3$—CH$_2$ | 3 | S | 4-CH$_3$-Ph | 78-81$^f$ | 73 |
| 172 | CH$_3$—CH$_2$ | CH$_3$ | 3 | S | 4-CH$_3$-Ph | 86-8$^f$ | 52 |

$^a$= Recrystallization solvent;
$^b$= Referred to the recrystallized product;
$^f$= diisopropylether;
$^j$= n-hexane/ethyl acetate (1:1).

PHARMACOLOGICAL STUDIES

STUDIES WITH WASHED PLATELETS: Aggregation

The suspensions of washed platelets were obtained from rabbit's blood (male, albino, New Zealand), anticoagulated with a solution of citric acid citrate/sodium dextrose in the ratio 1:6 (v:v).

The platelet rich plasma (PRP) was obtained by centrifuging blood samples at 100×g for 10 minutes and the platelets by centrifuging the PRP at 1,800×g for 15 minutes at 4° C. The pellet obtained in this way was washed twice with Tyrode tampon containing citric acid, PGE and aspirase, pH 6.5. The platelets so-washed were finally resuspended in Hepes-Tyrode tampon, pH 7.35 supplemented with bovine seric albumin at 0.35%; Ca++ 2 mM.

The final platelet concentration was adjusted to 300,000 platelets/mic-1. The aggregation was measured turbidimetrically using a lumiaggregometre (Chrono-Log.Co; Haventon, Pa., USA) at 37° C. under stirring at 1,100 r.p.m. The study was made in aliquots of preincubated PRP, with the compounds under study, for 5 minutes. The concentration of the antagonists was, in all cases, between 10 micM and 0.1 micM. The aggregation was induced by adding L-PAF diluted in 5 micl of Hepes/albumin tampon, the final concentration being 1.9×0,000000001. The IC50 for each compound was evaluated graphically from the dose-response curves.

TABLE 1

Effect on the aggregation induced by 1-PAF in rabbit platelets.

| Compound according to example | IC$_{50}$ (μM) |
|---|---|
| 1 | 0.34 |
| 2 | 1.1 |
| 3 | 0.24 |
| 4 | 0.85 |
| 5 | 1.3 |
| 6 | 3.0 |
| 13 | 2.3 |
| 30 | 3.1 |
| 41 | 2.7 |
| 45 | 0.15 |
| 46 | 1.40 |
| 48 | 4.0 |
| 52 | 2.7 |
| 61 | 2.0 |
| 62 | 10.0 |
| 64 | 2.8 |
| 66 | 2.4 |
| 74 | 2.8 |
| 76 | 2.8 |
| 82 | 2.8 |
| 110 | 4.3 |
| 113 | 3.0 |
| 131 | 10.0 |
| 133 | 2.4 |
| 135 | 2.8 |
| 139 | 0.70 |
| 140 | 2.0 |
| 152 | 3.0 |
| 154 | 1.1 |
| 163 | 0.41 |
| 164 | 0.32 |
| 165 | 2.5 |
| 166 | 2.6 |
| 167 | 0.40 |
| 172 | 0.19 |

The data reflected is the mean of three experiments performed in duplicate. Concentration of 1-PAF=1.92 nM.

The concentrations of compounds, in all cases, were between 10 and 0.1 micM.

We claim:

1. 4-alkyl-1,4-dihydropyridines with antagonistic activity of the PAF-acether, of formula (I);

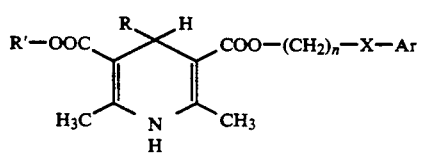

where:
R is a saturated alkyl chain of C1-C2;

R' is an alkyl chain of C1–C16, where the chain can be linear, branched, or, if greater than three carbons in length, cyclic; the chain can be saturated or, if greater than two carbons in length, unsaturated; and the chain can contain oxygen and/or nitrogen components;

n is a number that can be 2 or 3;

X defines an oxygen atom (O), or a sulphur (S), or a $SO_2$ group;

Ar represents an unsubstituted naphthyl ring or an unsubstituted or substituted phenyl ring, wherein the substituents are selected from the group consisting of 4-nitro, 4-acetylamino, 4-chloro, 3,4,-dichloro, 4-methyl, 4-methoxy, 3-dimethylamino, 4-phenyl, 4-phenoxy, and 4-benzyl; with the proviso that if X=S and n=2 then Ar must be a substituted phenyl ring.

2. The compound of claim 1 wherein R is methyl or ethyl.

3. The compound of claim 1 wherein R' is selected from the group consisting of methyl, ethyl, isopropyl, tertiary-butyl, n-hexyl, n-hexadecyl, allyl, 1-undecenyl, cinnamyl, 2-methoxyethyl, tetrahydrofurfuryl and 2(N-morpholine) ethyl.

4. The compound of claim 1 wherein Ar is selected from the group consisting of phenyl, 4-nitrophenyl, 4-acetylaminophenyl, 4-chlorophenyl, 3,4,-dichlorophenyl, 4-methylphenyl, 4-methoxyphenyl, 3-dimethyl-aminophenyl, 4-biphenyl, 4-phenoxyphenyl, 4-benzylphenyl, 4-benzyloxyphenyl, 1-naphthyl and 2-naphthyl.

* * * * *

UNITED STATES PATENT AND TRADEMARK OFFICE
CERTIFICATE OF CORRECTION

PATENT NO. : 5,298,619
DATED : March 29, 1994
INVENTOR(S) : Carlos SUNKEL et al.

It is certified that error appears in the above-indentified patent and that said Letters Patent is hereby corrected as shown below:

On the title page:

delete the Foreign Application Priority Data, and substitute therefor:

[30] Foreign Application Priority Data

Sep. 9, 1991 [EPO] Europe ........ 91500103

Signed and Sealed this

Fifteenth Day of November, 1994

Attest:

BRUCE LEHMAN

*Attesting Officer*   *Commissioner of Patents and Trademarks*